United States Patent
Arnott et al.

(10) Patent No.: US 6,662,627 B2
(45) Date of Patent: Dec. 16, 2003

(54) PHOTOACOUSTIC INSTRUMENT FOR MEASURING PARTICLES IN A GAS

(75) Inventors: William Patrick Arnott, Reno, NV (US); Hans Moosmuller, Reno, NV (US); John W. Walker, Pueblo, CO (US)

(73) Assignee: Desert Research Institute, Reno, NV (US)

(*) Notice: Subject to any disclaimer, the term of this patent is extended or adjusted under 35 U.S.C. 154(b) by 72 days.

(21) Appl. No.: 09/888,251

(22) Filed: Jun. 22, 2001

(65) Prior Publication Data

US 2002/0194897 A1 Dec. 26, 2002

(51) Int. Cl.[7] .............................................. G02N 21/00
(52) U.S. Cl. .................... 73/24.02; 73/24.06; 73/28.01; 356/438; 356/440
(58) Field of Search ............................. 73/24.02, 24.01, 73/24.03, 24.06, 23.33, 28.01, 643; 356/432, 433, 438, 440, 437

(56) References Cited

U.S. PATENT DOCUMENTS

| | | | |
|---|---|---|---|
| 4,044,257 A | * 8/1977 | Kreuzer ....................... 250/344 |
| 4,234,258 A | * 11/1980 | Frosch et al. ................ 356/437 |
| 4,399,689 A | 8/1983 | Bechthold et al. .......... 73/24.02 |
| 4,412,445 A | * 11/1983 | Spellicy ...................... 73/24.02 |
| 4,436,428 A | 3/1984 | Watanabe et al. |
| 4,594,004 A | * 6/1986 | Ishida et al. ................. 356/433 |
| 4,740,086 A | 4/1988 | Oehler et al. |
| 4,818,882 A | 4/1989 | Nexo et al. |
| 4,893,934 A | 1/1990 | Hansen |
| 5,069,551 A | 12/1991 | Brown |
| 5,159,411 A | 10/1992 | Hammerich et al. |
| 5,339,674 A | 8/1994 | Hammerich et al. |
| 5,540,079 A | 7/1996 | Brown et al. |
| 5,616,826 A | * 4/1997 | Pellaux et al. ............. 73/24.02 |
| 5,841,017 A | 11/1998 | Baraket et al. |
| 5,933,245 A | 8/1999 | Wood et al. |
| 6,006,585 A | 12/1999 | Forster |
| 6,031,233 A | 2/2000 | Levin et al. |
| 6,082,178 A | 7/2000 | Berstein et al. |
| 6,108,096 A | 8/2000 | Ushio et al. |

FOREIGN PATENT DOCUMENTS

| JP | 06194343 A | * 7/1994 | ................. 356/437 |
| WO | WO 99/15879 | 4/1999 | |

OTHER PUBLICATIONS

Arnott, W.P. et al. "Thermoacoustic enhancement of photoacoustic spectroscopy: Theory and measurements of the signal to noise ratio" Rev. Sci. Instrum. Oct. 1995, vol 66, No. 10, pp. 4827–4833.*

H. Moosmuller, W.P. Arnott, C.F. Rogers, J.C. Chow, and C.A. Frazier, "Photoacoustic and filter measurments related to aerosol light absorption during the Northern Front Range Air Quality Study," Journal of Geophysical Research, American Geophysical Union (United States), vol. 103 (No. D21), p. 28, 149–28, (Jun. 26, 1998).

* cited by examiner

Primary Examiner—Edward Lefkowitz
Assistant Examiner—Michael Cygan
(74) Attorney, Agent, or Firm—Ryan A. Heck; Ian F. Burns & Assoc.

(57) ABSTRACT

A photoacoustic sensor that measures carbon black particles emitted in the exhaust gas of a vehicle traveling on a road or being tested on a dynamometer or engine stand. The sensor includes an acoustic waveguide and a pump mounted to an outlet of the waveguide. The pump pulls the gas through the waveguide. A critical orifice is mounted between the pump and the outlet. The critical orifice prevents noise generated by the pump from entering the waveguide. Optical windows are mounted at opposite ends of the waveguide. A modulated source of light is located adjacent one of the windows and irradiates the waveguide. A microphone is attached to the waveguide. The microphone detects an acoustic signal generated by absorption of the light by the particles in the gas. The acoustic signal is proportional to the mass concentration of particles in the gas. The microphone generates an electrical signal proportional to the acoustic signal.

32 Claims, 4 Drawing Sheets

PHOTOACOUSTIC INSTRUMENT FOR MEASURING PARTICLES IN A GAS

BACKGROUND OF THE INVENTION

1. Field of Invention

This invention relates to a photoacoustic instrument or sensor for measuring particulate emissions from vehicles and other combustors. It can be placed at a roadside location. The instrument is also used as a primary method for quantitatively measuring aerosol light absorption in the atmosphere.

2. Description of Related Art

Internal combustion engines used to power vehicles generate both gaseous and particulate emissions as they travel on roads and expressways. The gaseous emissions have been extensively sampled and tested. Particulate emissions have proven to be more difficult to sample and test at a roadside location. Photo-acoustic gas sensors have been used to detect concentrations of gases such as carbon monoxide and other hydrocarbons. Photo-acoustic gas sensors generate an acoustic pressure wave when the gas is irradiated with a modulated light source in a sample chamber. The radiation absorbed by the gas results in pressure variations in a given volume of gas. The pressure variation is proportional to the amount of energy absorbed. A microphone can detect the pressure wave. The magnitude of the wave is proportional to the concentration of the gas. The acoustic pressure wave arises as the gas absorbs the optical radiation and is heated. Periodic thermal expansion and pressure fluctuations result, corresponding to the modulation of the optical radiation. Measurement of the acoustic pressure then permits inferring the gas concentration. Different gases are characterized by the use of light waves of different wavelengths corresponding to the absorption wavelength of the gas being tested.

Photoacoustic sensors have a high degree of measurement sensitivity and have to be carefully designed in order to prevent external noise from generating erroneous results. One problem that occurs with photoacoustic sensors is that they can receive acoustic signals (noise) from outside the sample chamber. This noise enters the sensor through the same entrance as the sample gas. The external acoustic noise causes false readings.

Another problem with photoacoustic sensors is that they can drift out of calibration due to changing pressure on the microphone. Typical microphones have an electrically conducting membrane and a fixed back plate. If air is moving in the test chamber, the pressure on the membrane can be different than the pressure on the back plate causing the sensor to go out of calibration.

Another problem with photoacoustic sensors is that the light source has to be aligned with the sample chamber to obtain accurate readings. If the light source is an infrared laser, it cannot be visually aligned. For safety reasons, it is desirable to enclose the laser so that the laser cannot accidentally contact an eye.

A current unmet need exists for a roadside particulate emission sensor that is not influenced by external noise, that is readily calibrated, that stays in calibration and that has an easily alignable light source.

SUMMARY OF INVENTION

1. Advantages of the Invention

An advantage of the present invention is that it provides a sensor for detecting particulate emissions at a roadside location.

Another advantage of the present invention is that it provides a photoacoustic instrument that can measure black carbon particles.

A further advantage of the present invention is that it provides a photoacoustic sensor that uses cameras to align a laser beam.

An additional advantage of the present invention is that it provides a photoacoustic sensor that prevents external noise from generating erroneous results.

Yet another advantage of the present invention is that it provides a photoacoustic sensor that prevents calibration drift due to changing pressure on a microphone.

A further advantage of the present invention is that it provides a photoacoustic sensor that is compact and easily transported.

A further advantage of the present invention is that it provides a photoacoustic sensor that is easily calibrated.

These and other advantages of the present invention may be realized by reference to the remaining portions of the specification, claims, and abstract.

2. Brief Description of the Invention

The present invention comprises a photoacoustic sensor for measuring light absorbing particles in a gas. The most common particles sampled are black carbon or soot, though the choice of light wavelength allows other particles to be sampled. The photoacoustic sensor comprises an acoustic waveguide and a modulated source of light located in proximity to the waveguide. The modulated light irradiates the particle-laden gas in the waveguide. A microphone is attached to the waveguide. The microphone detects an acoustic signal generated by absorption of the light by the particles in the gas. The acoustic signal is proportional to the mass concentration of particles in the gas. A pump is mounted to the waveguide. The pump pulls the gas through the waveguide. A piezoelectric calibrator is mounted perpendicular to the waveguide. The piezoelectric calibrator provides a known acoustic signal for calibrating the sensor. A critical orifice is mounted between the pump and the waveguide. The critical orifice prevents noise generated by the pump from entering the waveguide. Helmholtz resonators are mounted to the sample inlet of the waveguide. The [helmholtz]Helmholtz resonator prevents unwanted noise frequencies from entering the waveguide. A pressure equalizer is mounted between the critical orifice and the microphone. The pressure equalizer equalizes the pressure in proximity of the microphone.

The above description sets forth, rather broadly, the more important features of the present invention so that the detailed description of the preferred embodiment that follows may be better understood and contributions of the present invention to the art may be better appreciated. There are, of course, additional features of the invention that will be described below and will form the subject matter of claims. In this respect, before explaining at least one preferred embodiment of the invention in detail, it is to be understood that the invention is not limited in its application to the details of the construction and to the arrangement of the components set forth in the following description or as illustrated in the drawings. The invention is capable of other embodiments and of being practiced and carried out in various ways. Also, it is to be understood that the phraseology and terminology employed herein are for the purpose of description and should not be regarded as limiting.

DESCRIPTION OF THE PREFERRED EMBODIMENT

In the following detailed description of the preferred embodiments, reference is made to the accompanying drawings, which form a part of this application. The drawings show, by way it of illustration, specific embodiments in which the invention may be practiced. It is to be understood that other embodiments may be utilized and structural changes may be made with out departing from the scope of the present invention.

Photoacoustic Sensor

Figure 1:
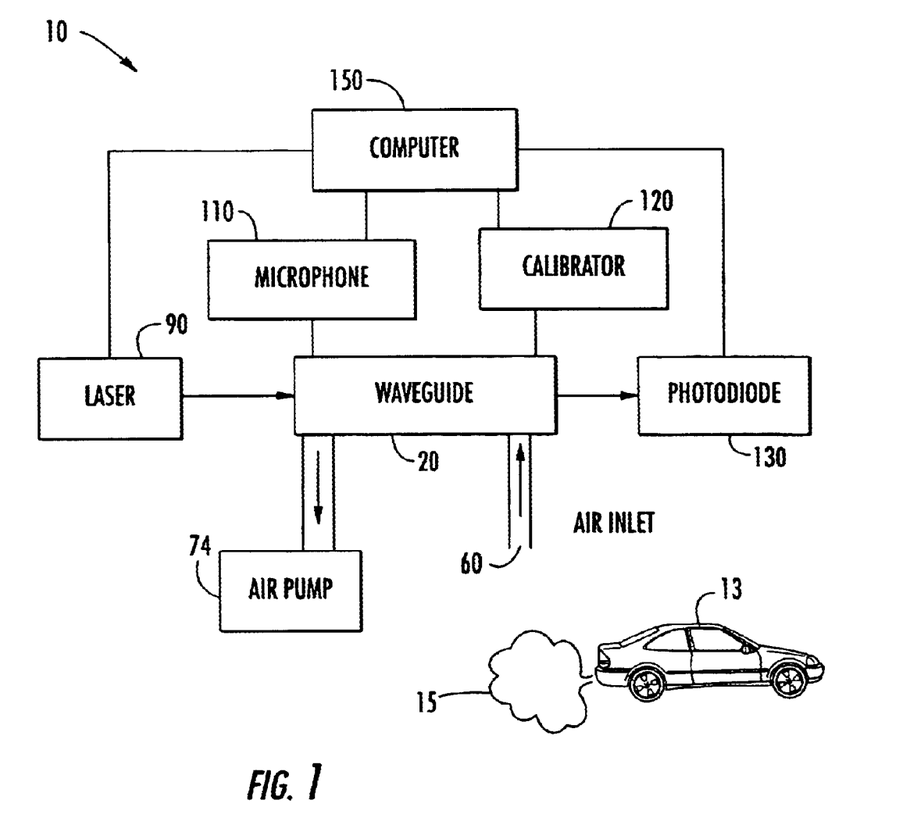
FIG. 1 is substantially a schematic diagram of a photoacoustic sensor in accordance with the present invention.

Referring to FIG. 1 schematic diagram of a photoacoustic instrument or sensor 10 for measuring particles in a gas is shown. A vehicle 13 using a fossil fuel generates an exhaust gas 15 that is diluted by the surrounding air. The exhaust gas contains entrained particulates such as black carbon particles. Sensor 10 is used to measure the particles in the air. Sensor 10 comprises an acoustic waveguide 20, an air pump 74, an air inlet 60, laser 90, a microphone assembly or acoustic sensor 110, a piezoelectric calibrator 120, a photodiode 130 and a computer 150. The gas 15 is pulled into the waveguide 20 by pump 74. The laser 90 passes a laser beam through the waveguide 20 where it is received by photodiode 130. When the laser impinges on a particle, it generates an acoustical pressure that can be measured by microphone 110. A computer 150 receives an electrical signal from the microphone and can calculate the quantity of particles in the gas. The computer is attached to the photodiode and the laser. The computer controls the pulse rate of the laser. A calibrator 120 is attached to the waveguide and is controlled by the computer. The calibrator generates a known acoustic signal.

Figure 2:
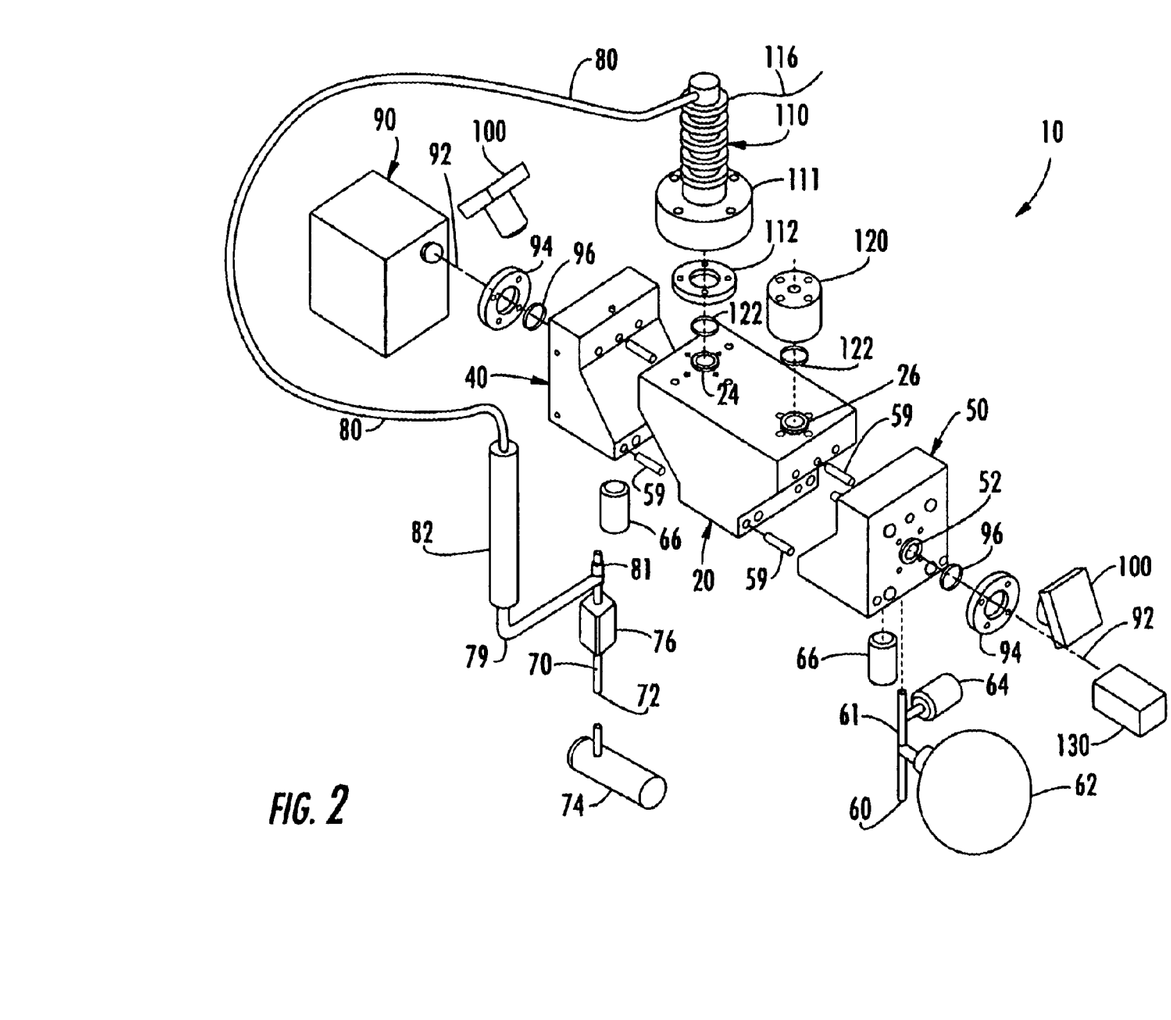
FIG. 2 is substantially an exploded perspective view of a photoacoustic sensor in accordance with the present invention.
Figure 3:
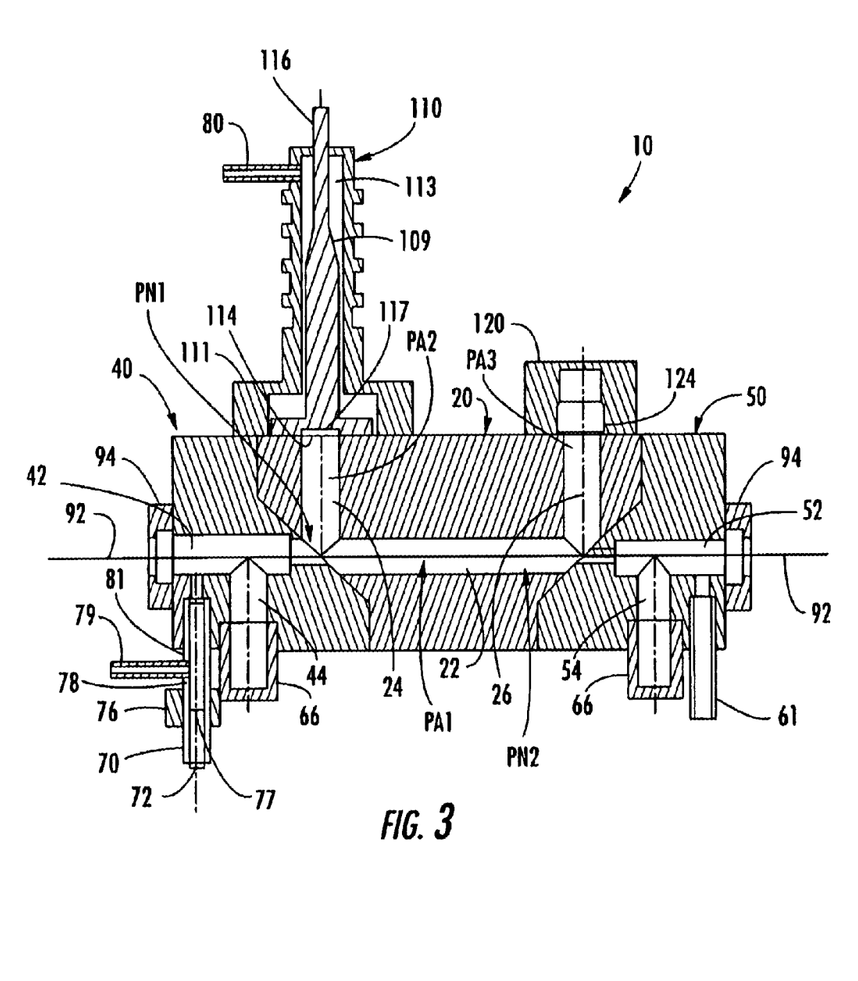
FIG. 3 is substantially an assembled side cross-sectional view of the photoacoustic sensor of FIG. 2.

With reference to FIGS. 2 and 3, more details of the photoacoustic instrument or sensor 10 for measuring particles in a gas are shown. Sensor 10 further comprises an acoustic waveguide 20, left and right coupling sections 40 and 50, a pump 74, a low frequency acoustic bandstop filter 62, a high frequency acoustic bandstop filter 64, a critical orifice 76, a microphone assembly 110, a laser 90, windows 94, a pair of cameras 100, and a piezoelectric calibrator 120.

Waveguide 20 has a waveguide cavity 22 that passes through waveguide 20. In the preferred embodiment, a microphone bore 24 intersects waveguide cavity 22 at a right angle or is perpendicular to the waveguide cavity. A calibrator bore 26 also preferably intersects waveguide cavity 22 at a right angle. Bores 24 and 26 are located at pressure nodes PN1 and PN2. The pressure nodes allow the bores to have a minimal effect on the resonator or cavity acoustics.

First coupling section 40 has a bore 42 passing through and a de-tuning bore 44 that intersects bore 42 at a right angle. Similarly, second coupling section 50 has a bore 52 passing through and a de-tuning bore 54 that intersects bore 52 at a right angle. First and second coupling sections 40 and 50 are attached to waveguide 20 using alignment pins 59. One half of alignment pins 59 rests in an aperture in the coupling section and the other half in an aperture in the waveguide. The coupling sections are affixed to the waveguide by bolts or other attachment devices (not shown). The waveguide and coupling sections are preferably formed out of aluminum. A block of aluminum can be milled and bored to form the waveguide and coupling sections. Other metals and manufacturing techniques could also be used. Several tubes could also be joined together to form the waveguide and coupling sections.

De-tuning cavities 66 are attached to de-tuning bores 44 and 54. The de-tuning cavities 66 serve to reduce the coupling of acoustic noise into the waveguide cavity at the acoustic resonance frequency of the cavity.

A pump 74 is attached to an air outlet 72. An outlet pipe 70 connects pump 74 to a critical orifice 76. Critical orifice 76 comprises a hole 77 in a disc 78 mounted in the path of airflow. The speed of air flowing through the orifice approaches the speed of sound in the gas. The orifice is deemed critical when the pump pressure is sufficient to make the flow rate approach the speed of sound. Sound from the pump that would normally travel into the waveguide is reflected at the critical orifice back toward the pump, thereby preventing the sound from interfering with measurements in cavity 22. The critical orifice is commercially available from Okeefe Controls. The critical orifice is attached to bore 42 by pipe 81.

A microphone assembly 110 is mounted to waveguide 20. Microphone assembly 110 includes a microphone 109 contained in a microphone enclosure 111. Enclosure 111 is attached by a microphone mount 112 to waveguide 20. A seal 122 seals the microphone. The microphone comprises a microphone cavity 113, a flexible membrane 114 that faces into bore 24 and a fixed metallic back plate 117. Membrane 114 and back plate 117 form a parallel plate capacitor. A wire 116 provides an electrical signal from the microphone. The microphone assembly is commercially available from ACO Pacific.

An equalizer tube 80 is connected above the critical orifice by an equalizer pipe 79. Equalizer tube 80 is connected to microphone cavity 113. Since the microphone has a movable electrically conducting membrane 114 facing into the acoustical waveguide, and a fixed metallic back plate 117, to form a parallel plate capacitor, acoustical signals produced by the resonator force the movable membrane to change position with respect to the back plate thereby changing the capacitance. Since the waveguide has a continuous air sample being pulled through the waveguide, the static pressure on the movable membrane could be different from that on the backplate causing a drift of the microphone calibration and false measurements. The equalization tube and line prevents this pressure change and accompanying calibration drift. The equalization tube may contain a drying agent (not shown) in drying section 82. The drying agent removes water vapor in the air. The water vapor could condense between the back plate and movable membrane of the microphone causing it to short out or the water vapor could condense on the preamplifier electronics in the microphone causing them to fail. The preferred drying agent is Dryerite available from Cole-Palmer.

An air sample inlet 60 admits sample air into the waveguide. Inlet 60 is at the end of inlet pipe 61. Inlet pipe 61 is connected to bore 52. A low frequency acoustic band stop filter or resonator 62 and a high frequency filter 64 are attached to inlet pipe 61. Low frequency filter 62 is a Helmholtz resonator. A [helmholtz]Helmholtz resonator is an enclosed volume such as a metal sphere with a tube extending from the sphere to the inlet pipe. Helmholtz resonators reflect sound of certain wavelengths depending upon the dimensions of the resonator. Helmholtz resonator 62 rejects frequencies well below the resonant frequency of the acoustic waveguide. Resonator 62 rejects unwanted noise from outside the instrument that enters through the inlet 60. Similarly, filter 64 rejects higher frequency noise from outside the instrument.

A laser 90 is aligned with windows 94. A seal 96 seals window 94 to the coupling sections. Laser 90 generates a laser beam 92. Laser 90 is preferably a 532 nm or 1047 nm unit available from Crystalaser. Laser beam 92 passes through window 94 and bore 42 into waveguide cavity 22 and irradiates the gas containing particles therein. The laser beam then passes through bore 52 and window 94. Photodetector 130 receives the laser beam at the other end of waveguide 20. A pair of cameras 100 is mounted to view each of the windows 94. Cameras 100 are miniature pinhole black and white cameras commercially available from RadioShack. Cameras 100 are focused on windows 94. Since laser 90 can be an infrared laser, aligning the laser visually is impossible. Since laser safety concerns may make it necessary to completely enclose the laser beam in an enclosure, the laser beam height, lateral orientation and tilt can be monitored and adjusted by the operator while safely viewing the laser beam position on a monitor. The laser is aligned when it is in the center of the window.

A piezoelectric calibrator 120 is mounted to waveguide 20 above calibrator bore 26. A seal 122 is used to seal calibrator 120 to the waveguide. Piezoelectric calibrator 120 has a piezoelectric element 124 adjacent bore 26. Piezoelectric calibrator element 124 is commercially available from RadioShack. The piezoelectric element is turned on in an alternating fashion between measurements. The piezoelectric element sends a known acoustic signal into the waveguide in order to obtain acoustic calibration of the resonator cavity (resonance frequency and quality factor). Other calibration sources such as a speaker can be used to generate a known acoustic signal

Operation

The waveguide cavity 22 is a full wavelength resonator with pressure nodes PN1 and PN2 at the ends of cavity 22 and a pressure antinode PA1 at the center. A pressure node is a region of very low acoustic pressure. A pressure antinode is a region of highest acoustic pressure in the acoustic standing wave in the waveguide cavity. Where the coupling sections 40 and 50 join the waveguide 20, the mating surfaces are angled or sloped at 45 degrees to accommodate insertion of the laser beam. The pressure nodes PN1 and PN2 are located where the laser enters the waveguide cavity 22. The diameter of bores 42 and 52 is much smaller than the acoustic wavelength and along with being located at the pressure nodes allows the bores to have a minimal effect on the resonator or cavity acoustics. Laser beam 92 is modulated at the acoustic resonance frequency of the waveguide so that sound produced by light absorption is amplified by the waveguide resonance. This arrangement also helps to reduce the coupling of noise into the resonator at the acoustic frequency since holes are at the pressure nodes. The microphone element 114 is located at a pressure antinode PA2 at the end of microphone bore 24. The piezoelectric calibrator is located at a pressure antinode PA3 at the end of calibrator bore 26.

Figure 4:
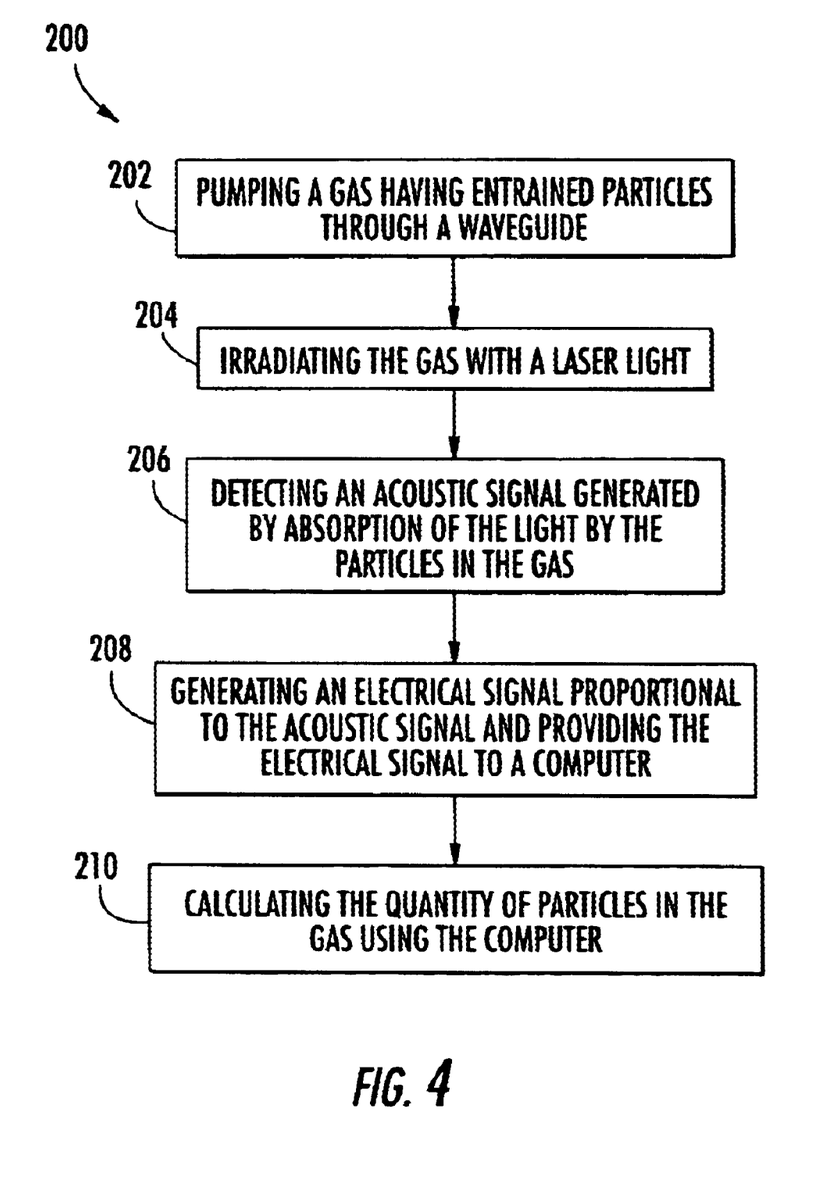
FIG. 4 is substantially a flowchart showing the operation of the photoacoustic sensor.

Referring to FIG. 4, a flowchart 200 of the operation of photoacoustic instrument is shown. First at step 202, sample gas containing black carbon particles is continuously pulled through the waveguide cavity 22 by pump 74. The air flows into inlet 60 and is expelled from the pump. Next, at step 204, the laser passes through window 94, through bore 42, waveguide cavity 22, bore 52, window 94 and is received by photodetector 130. The laser beam power amplitude and phase at the modulation frequency are obtained from photodetector 130. The modulation frequency is the resonance frequency of the acoustic waveguide.

As the gas containing black carbon particles is irradiated with the laser, the heat from light absorption transfers from the particles to the surrounding air and an acoustic pressure wave or sound wave is generated. The sound is generated near the center of waveguide cavity 22 in the region of the pressure antinode PA1. The radiation absorbed by the black carbon particles results in pressure variations in a given volume. The pressure variation is proportional to the amount of energy absorbed. The pressure wave is detected by microphone 109 at step 206. The magnitude of the wave is proportional to the amount of light absorption and amount of laser power. From the amount of light absorption, the concentration of particles can be determined. The microphone 109 generates an electrical signal that is proportional to the mass concentration of particles at step 208. The electrical signal is provided to an amplifier (not shown) and computer 150 through wire 116. The computer calculates, at step 210, the concentration of the carbon black particles as well as the amount of light that is being absorbed or blocked by the carbon black particles in the air. The piezoelectric element 124 generates a known acoustic signal to calibrate the sensor. Calibration is performed between light absorption measurements.

Phase sensitive detection is used for processing of the electronic signals that control the laser beam power modulation and the microphone and photodiode signals. Phase sensitive detection can be accomplished with an appropriately configured lock-in amplifier. It can also be accomplished using an analog to digital converter with hardware trigger and laser beam power modulation controlled by an on-board counter/timer. The noise floor of the measurement can be determined from the weighted average of the electrical signal within the resonance response curve, excluding the signal exactly at the modulation frequency (resonance frequency of the waveguide).

The computer uses an algorithm to process the electrical signal. The algorithm calculates light absorption that is proportional to the quantity of particles. The light absorption is calculated using the acoustic pressure measured with the microphone, the resonator quality factor, the resonant frequency, the Fourier component of the laser beam power and the cross sectional area of the waveguide.

Photoacoustic sensor 10 is readily packaged such that it is easily transportable to a roadside location. Sensor 10 only needs to be connected to a standard source of ac power in order to operate. At a roadside location, sensor 10 is able to monitor the amount of soot in the air. Sensor 10 measures light absorption and the mass concentration of black carbon entrained in air.

Typical uses of the photoacoustic sensor are to measure the absorption component of viewing range and clarity degradation in cities or National Parks. The climatic influence of black carbon on the absorption of sunlight can be studied with the sensor. The mass concentration measurement can be used to quantify the black carbon produced by the burning of engine fuels and diesel fuel as an example.

Conclusion

The present invention solves many of the problems associated with the prior art. The present invention provides a sensor for detecting particulate emissions at a roadside location and in particular black carbon particles. The present invention also provides a photoacoustic sensor that uses cameras to align a laser beam and that prevents external noise from generating erroneous results. The present invention further provides a photoacoustic sensor that prevents calibration drift due to changing pressure on the microphone.

Although the description above contains many specifications, these should not be construed as limiting the scope of the invention but as merely providing illustrations of some of the presently preferred embodiments of this invention. Thus, the scope of the invention should be determined by the appended claims and their legal equivalents rather than by the examples given.

What is claimed is:

1. A photoacoustic instrument for measuring particles in a gas, the sensor comprising:
   (A) an acoustic waveguide having an inlet for admitting the gas into the waveguide and an outlet for removing the gas from the waveguide;
   (B) a pump mounted to the outlet of the waveguide, the pump adapted to pull the gas through the waveguide;
   (C) a laser located adjacent the waveguide, the laser irradiating the waveguide with light the light traveling from the laser through the waveguide;
   (D) a first and second window attached to opposite ends of the waveguide, a first camera focused on the first window and a second camera focused on a second window, the cameras adapted to align the light, the light being aligned when the light is centered in the windows; and
   (E) a microphone attached to the waveguide, the microphone detecting an acoustic signal generated by absorption of the light by the particles in the gas, the acoustic signal proportional to the mass concentration of particles in the gas, the microphone generating an electrical signal proportional to the acoustic signal.

2. The photoacoustic instrument according to claim 1, wherein a piezoelectric calibrator is mounted perpendicular to the waveguide, the piezoelectric calibrator adapted to provide a known acoustic signal for calibrating the sensor.

3. The photoacoustic instrument according to claim 1, wherein a Helmholtz resonator is mounted to the inlet, the Helmholtz resonator adapted to prevent unwanted noise frequencies from entering the waveguide and a critical orifice is mounted between the pump and the outlet, the critical orifice adapted to prevent noise generated by the pump from entering the waveguide.

4. The photoacoustic instrument according to claim 1, wherein a pressure equalizer is mounted between the waveguide and the microphone, the pressure equalizer adapted to equalize pressure in proximity of the microphone.

5. The photoacoustic instrument according to claim 1, wherein a computer is attached to the microphone and receives an electrical signal generated by the microphone, the computer adapted to control the laser and to calculate the quantity of particles in the gas.

6. The photoacoustic instrument according to claim 1, wherein the laser is modulated at the acoustic resonance frequency of the waveguide so that sound produced by light absorption is amplified by the waveguide resonance.

7. The photoacoustic instrument according to claim 1, wherein the microphone is located at a pressure antinode.

8. The photoacoustic instrument according to claim 2, wherein a calibrator is located at a pressure antinode.

9. The photoacoustic instrument according to claim 1, wherein the laser light enters and exits the waveguide at a pressure node.

10. A photoacoustic sensor for measuring particles in a gas, the sensor comprising:
    (A) an acoustic waveguide adapted to hold a gas;
    (B) a modulated source of light located in proximity to the waveguide, the modulated light irradiating the waveguide;
    (C) an acoustic sensor attached to the waveguide, the sensor adapted to detect an acoustic signal generated by absorption of the light by the particles in the gas, the acoustic signal being proportional to the mass concentration of light absorbing particles in the gas;
    (D) a pump mounted to the waveguide, the pump adapted to draw the gas through the waveguide, wherein a critical orifice is mounted between the pump and the waveguide, the critical orifice adapted to prevent noise generated by the pump from entering the waveguide, and wherein a pressure equalizer is mounted between the critical orifice and the acoustic sensor, the pressure equalizer adapted to equalize pressure in proximity of the acoustic sensor; and
    (E) a calibrator mounted to the waveguide, the calibrator adapted to provide a known acoustic signal for calibrating the sensor.

11. The photoacoustic sensor according to claim 10, wherein a drying agent is located in the pressure equalizer, the drying agent adapted to remove water vapor from the gas.

12. A photoacoustic sensor for measuring particles in a gas, the sensor comprising:
    (A) an acoustic waveguide adapted to hold a gas, wherein a first and second window is mounted at each end of the waveguide;
    (B) a modulated source of light located in proximity to the waveguide, the modulated light irradiating the waveguide, wherein the light source is a laser adjacent one of the windows, the laser operable to provide the source of light, the light traveling from the laser through the window into the waveguide, wherein a first camera is focused on the first window and a second camera is focused on a second window, the cameras operable to align the source of light, the light being aligned when the light is centered in the windows;
    (C) an acoustic sensor attached to the waveguide, the sensor adapted to detect an acoustic signal generated by absorption of the light by the particles in the gas, the acoustic signal being proportional to the mass concentration of light absorbing particles in the gas;
    (D) a pump mounted to the waveguide, the pump adapted to draw the gas through the waveguide; and
    (E) a calibrator mounted to the waveguide, the calibrator adapted to provide a known acoustic signal for calibrating the sensor.

13. A photoacoustic instrument for measuring particles in a gas, the instrument comprising:
    (A) an acoustic waveguide having an inlet for admitting a gas into the waveguide and an outlet for removing the gas from the waveguide, wherein a piezoelectric calibrator is mounted perpendicular to the waveguide, the piezoelectric calibrator adapted to provide a known acoustic signal for calibrating the sensor;
    (B) a pump mounted to the outlet of the waveguide, the pump adapted to pull the gas through the waveguide;

(C) a critical orifice mounted between the pump and the outlet, the critical orifice adapted to prevent noise generated by the pump from entering the waveguide;

(D) a modulated source of light located adjacent the waveguide, the modulated light irradiating the waveguide, the light traveling from the source through the waveguide; and (E) a microphone attached to the waveguide, the microphone detecting an acoustic signal generated by absorption of the light by particles in the gas, the acoustic signal proportional to the mass concentration of particles in the gas, the microphone generating an electrical signal proportional to the acoustic signal.

14. A photoacoustic instrument for measuring particles in a gas, the instrument comprising:

(A) an acoustic waveguide having an inlet for admitting a gas into the waveguide and an outlet for removing the gas from the waveguide;

(B) a pump mounted to the outlet of the waveguide, the pump adapted to pull the gas through the waveguide;

(C) a critical orifice mounted between the pump and the outlet, the critical orifice adapted to prevent noise generated by the pump from entering the waveguide;

(D) a modulated source of light located adjacent the waveguide, the modulated light irradiating the waveguide, the light traveling from the source through the waveguide; and (E) a microphone attached to the waveguide, the microphone detecting an acoustic signal generated by absorption of the light by particles in the gas, the acoustic signal proportional to the mass concentration of particles in the gas, the microphone generating an electrical signal proportional to the acoustic signal, wherein a pressure equalizer is mounted between the waveguide and the microphone, the microphone having a flexible membrane and a fixed back plate, the pressure equalizer adapted to equalize pressure on the flexible membrane.

15. The photoacoustic instrument according to claim 14, wherein a drying agent is located in the pressure equalizer, the drying agent adapted to remove water vapor from the gas.

16. A photoacoustic instrument for measuring particles in a gas, the instrument comprising:

(A) an acoustic waveguide having an inlet for admitting a gas into the waveguide and an outlet for removing the gas from the waveguide;

(B) a pump mounted to the outlet of the waveguide, the pump adapted to pull the gas through the waveguide;

(C) a critical orifice mounted between the pump and the outlet, the critical orifice adapted to prevent noise generated by the pump from entering the waveguide;

(D) a modulated source of light located adjacent the waveguide, the modulated light irradiating the waveguide, the light traveling from the source through the waveguide, wherein the waveguide has a first and second window, a first camera is focused on the first window and a second camera is focused on a second window, the cameras operable to align the source of light, the light being aligned when the light is centered in the windows; and (E) a microphone attached to the waveguide, the microphone detecting an acoustic signal generated by absorption of the light by particles in the gas, the acoustic signal proportional to the mass concentration of particles in the gas, the microphone generating an electrical signal proportional to the acoustic signal.

17. The photoacoustic instrument according to claim 16, wherein the particles are black carbon and the gas is air, the instrument operable to measure a mass concentration of the black carbon particles in the air.

18. The photoacoustic instrument according to claim 17, wherein the instrument is located adjacent a road for measuring the particles emitted from passing vehicles.

19. A method of measuring particles in a gas comprising:

(A) providing a photoacoustic sensor, the photoacoustic sensor having an acoustic waveguide, the acoustic waveguide having an inlet and an outlet;

(B) pumping a gas from the inlet through the waveguide to the outlet and through a critical orifice, the critical orifice adapted to prevent noise from entering the waveguide through the outlet;

(C) irradiating the gas in the waveguide;

(D) detecting an acoustic signal generated by absorption of the light by the particles in the gas, the acoustic signal proportional to the quantity of particles in the gas, the microphone generating an electrical signal proportional to the acoustic signal; and (E) equalizing pressure between the back plate and front surface of the microphone.

20. A method of measuring particles in a gas comprising:

(A) providing a photoacoustic sensor, the photoacoustic sensor having an acoustic waveguide, the acoustic waveguide having an inlet and an outlet;

(B) pumping a gas from the inlet through the waveguide to the outlet and through a critical orifice, the critical orifice adapted to prevent noise from entering the waveguide through the outlet;

(C) irradiating the gas in the waveguide;

(D) detecting an acoustic signal generated by absorption of the light by the particles in the gas, the acoustic signal proportional to the quantity of particles in the gas, the microphone generating an electrical signal proportional to the acoustic signal; and (E) aligning the source of light using a camera, the light being aligned when the light is centered in the windows.

21. A photoacoustic sensor for measuring particles in a gas, the sensor comprising:

(A) an acoustic waveguide adapted to hold a gas and having an inlet to admit the gas;

(B) a modulated source of light located in proximity to the waveguide, the modulated light irradiating the waveguide;

(C) a microphone attached to the waveguide, the microphone adapted to detect an acoustic signal generated by absorption of the light by the particles in the gas, the acoustic signal being proportional to the concentration of particles in the gas;

(D) a pump mounted to the waveguide, the pump adapted to draw the gas through the waveguide, wherein a critical orifice is mounted between the pump and the waveguide, the critical orifice adapted to prevent noise generated by the pump from entering the waveguide, and wherein a pressure equalizer is mounted between the critical orifice and the microphone, the pressure equalizer adapted to equalize pressure in proximity of the microphone; and (E) a Helmholtz resonator mounted to the inlet of the waveguide, the Helmholtz resonator adapted to prevent unwanted noise frequencies from entering the waveguide.

22. A photoacoustic sensor for measuring particles in a gas, the sensor comprising:
(A) an acoustic waveguide adapted to hold a gas and having an inlet to admit the gas;
(B) a modulated source of light located in proximity to the waveguide, the modulated light irradiating the waveguide, wherein a first and second window is mounted at each end of the waveguide, the modulated source of light adjacent one of the windows, the light traveling from the modulated source through the window into the waveguide, and wherein a first camera is focused on the first window and a second camera is focused on a second window, the cameras operable to align the source of light, the light being aligned when the light is centered in the windows;
(C) a microphone attached to the waveguide, the microphone adapted to detect an acoustic signal generated by absorption of the light by the particles in the gas, the acoustic signal being proportional to the concentration of particles in the gas;
(D) a pump mounted to the waveguide, the pump adapted to draw the gas through the waveguide; and
(E) a Helmholtz resonator mounted to the inlet of the waveguide, the Helmholtz resonator adapted to prevent unwanted noise frequencies from entering the waveguide.

23. A photoacoustic instrument for measuring particles in a gas, the instrument comprising:
(A) an acoustic waveguide having an inlet for admitting a gas into the waveguide and an outlet for removing the gas from the waveguide;
(B) a pump mounted to the outlet of the waveguide, the pump adapted to pull the gas through the waveguide;
(C) a laser located adjacent the waveguide, the laser irradiating the waveguide with light, the light traveling from the laser through the waveguide;
(D) a microphone attached to the waveguide at a pressure antinode of the waveguide, the microphone detecting an acoustic signal generated by absorption of the light by the particles in the gas, the acoustic signal proportional to the mass concentration of particles in the gas, the microphone generating an electrical signal proportional to the acoustic signal; and
(E) a calibrator mounted to the waveguide at a pressure antinode of the waveguide, the calibrator adapted to provide a known acoustic signal for calibrating the instrument, wherein the calibrator is mounted at a right angle to the waveguide.

24. The photoacoustic instrument according to claim 23, wherein the calibrator is mounted at the end of a bore attached to the waveguide.

25. A photoacoustic instrument for measuring particles in a gas, the instrument comprising:
(A) an acoustic waveguide having an inlet for admitting a gas into the waveguide and an outlet for removing the gas from the waveguide;
(B) a pump mounted to the outlet of the waveguide, the pump adapted to pull the gas through the waveguide;
(C) a laser located adjacent the waveguide, the laser irradiating the waveguide with light, the light traveling from the laser through the waveguide;
(D) a microphone attached to the waveguide at a pressure antinode of the waveguide, the microphone detecting an acoustic signal generated by absorption of the light by the particles in the gas, the acoustic signal proportional to the mass concentration of particles in the gas, the microphone generating an electrical signal proportional to the acoustic signal, and wherein the microphone is mounted at a right angle to the waveguide; and
(E) a calibrator mounted to the waveguide at a pressure antinode of the waveguide, the calibrator adapted to provide a known acoustic signal for calibrating the instrument.

26. The photoacoustic instrument according to claim 25, wherein the microphone is mounted at the end of a bore attached to the waveguide.

27. A photoacoustic instrument for measuring particles in a gas, the instrument comprising:
(A) an acoustic waveguide having an inlet for admitting a gas into the waveguide and an outlet for removing the gas from the waveguide;
(B) a pump mounted to the outlet of the waveguide, the pump adapted to pull the gas through the waveguide;
(C) a laser located adjacent the waveguide, the laser irradiating the waveguide with light, the light traveling from the laser through the waveguide;
(D) a microphone attached to the waveguide at a pressure antinode of the waveguide, the microphone detecting an acoustic signal generated by absorption of the light by the particles in the gas, the acoustic signal proportional to the mass concentration of particles in the gas, the microphone generating an electrical signal proportional to the acoustic signal; and
(E) a calibrator mounted to the waveguide at a pressure antinode of the waveguide, the calibrator adapted to provide a known acoustic signal for calibrating the instrument, wherein the microphone and the calibrator are located at a pressure antinode.

28. A photoacoustic instrument for measuring particles in a gas, the instrument comprising:
(A) an acoustic waveguide having an inlet for admitting a gas into the waveguide and an outlet for removing the gas from the waveguide;
(B) a pump mounted to the outlet of the waveguide, the pump adapted to pull the gas through the waveguide, wherein a critical orifice is mounted between the pump and the waveguide, the critical orifice adapted to prevent noise generated by the pump from entering the waveguide;
(C) a laser located adjacent the waveguide, the laser irradiating the waveguide with light, the light traveling from the laser through the waveguide;
(D) a microphone attached to the waveguide at a pressure antinode of the waveguide, the microphone detecting an acoustic signal generated by absorption of the light by the particles in the gas, the acoustic signal proportional to the mass concentration of particles in the gas, the microphone generating an electrical signal proportional to the acoustic signal, wherein a pressure equalizer is mounted between the critical orifice and the acoustic sensor, the pressure equalizer adapted to equalize pressure in proximity of the acoustic sensor; and
(E) a calibrator mounted to the waveguide at a pressure antinode of the waveguide, the calibrator adapted to provide a known acoustic signal for calibrating the sensor.

29. The photoacoustic instrument according to claim 28, wherein a drying agent is located in the pressure equalizer, the drying agent adapted to remove water vapor from the gas.

30. A photoacoustic instrument for measuring particles in a gas, the instrument comprising:
   (A) an acoustic waveguide having an inlet for admitting a gas into the waveguide and an outlet for removing the gas from the waveguide;
   (B) a pump mounted to the outlet of the waveguide, the pump adapted to pull the gas through the waveguide;
   (C) a laser located adjacent the waveguide, the laser irradiating the waveguide with light, the light traveling from the laser through the waveguide;
   (D) a microphone attached to the waveguide at a pressure antinode of the waveguide, the microphone detecting an acoustic signal generated by absorption of the light by the particles in the gas, the acoustic signal proportional to the mass concentration of particles in the gas, the microphone generating an electrical signal proportional to the acoustic signal, wherein the microphone has a fixed backplate and a flexible membrane, the pressure being equalized around the flexible membrane; and
   (E) a calibrator mounted to the waveguide at a pressure antinode of the waveguide, the calibrator adapted to provide a known acoustic signal for calibrating the instrument.

31. The photoacoustic instrument according to claim 30 wherein the flexible membrane faces into the waveguide.

32. A photoacoustic instrument for measuring particles in a gas, the instrument comprising:
   (A) an acoustic waveguide having an inlet for admitting a gas into the waveguide and an outlet for removing the gas from the waveguide;
   (B) a pump mounted to the outlet of the waveguide, the pump adapted to pull the gas through the waveguide;
   (C) a laser located adjacent the waveguide, the laser irradiating the waveguide with light, the light traveling from the laser through the waveguide, wherein a first and second window is mounted at each end of the waveguide, and wherein a first camera is focused on the first window and a second camera is focused on a second window, the cameras operable to align the light, the light being aligned when the light is centered in the windows;
   (D) a microphone attached to the waveguide at a pressure antinode of the waveguide, the microphone detecting an acoustic signal generated by absorption of the light by the particles in the gas, the acoustic signal proportional to the mass concentration of particles in the gas, the microphone generating an electrical signal proportional to the acoustic signal; and
   (E) a calibrator mounted to the waveguide at a pressure antinode of the waveguide, the calibrator adapted to provide a known acoustic signal for calibrating the instrument.

* * * * *